(12) United States Patent
Davis et al.

(10) Patent No.: US 10,729,557 B2
(45) Date of Patent: Aug. 4, 2020

(54) POROUS SURGICAL IMPLANT AND METHOD OF MAKING SAME

(71) Applicant: Warsaw Orthopedic, Inc., Warsaw, IN (US)

(72) Inventors: Darren L. Davis, Arlington, TN (US); Eric C. Lange, Collierville, TN (US); Anthony J. Melkent, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 16/107,581

(22) Filed: Aug. 21, 2018

(65) Prior Publication Data

US 2020/0060838 A1  Feb. 27, 2020

(51) Int. Cl.
*A61F 2/44* (2006.01)
*A61F 2/30* (2006.01)
*A61L 27/56* (2006.01)
*A61L 27/58* (2006.01)

(52) U.S. Cl.
CPC .......... *A61F 2/447* (2013.01); *A61F 2/30965* (2013.01); *A61L 27/56* (2013.01); *A61L 27/58* (2013.01); *A61F 2002/3092* (2013.01); *A61F 2210/0004* (2013.01); *A61L 2430/02* (2013.01)

(58) Field of Classification Search
CPC .................................................. A61F 2/30965
See application file for complete search history.

(56) References Cited

U.S. PATENT DOCUMENTS

| 6,942,698 | B1 * | 9/2005 | Jackson | A61F 2/4455 606/247 |
| 2003/0039676 | A1 * | 2/2003 | Boyce | A61B 17/0401 424/423 |
| 2009/0157194 | A1 * | 6/2009 | Shikinami | A61F 2/28 623/23.72 |
| 2011/0022180 | A1 | 1/2011 | Melkent et al. | |
| 2011/0045087 | A1 | 2/2011 | Kerr et al. | |
| 2012/0265306 | A1 * | 10/2012 | Trieu | A61F 2/447 623/17.16 |
| 2012/0312779 | A1 * | 12/2012 | Patterson | B23K 26/362 216/41 |
| 2015/0045904 | A1 | 2/2015 | Brax et al. | |

FOREIGN PATENT DOCUMENTS

| CN | 101450517 | 7/2011 |
| CN | 104706446 | 6/2015 |
| EP | 1433489 | 6/2004 |

OTHER PUBLICATIONS

International Search Report and Written Opinion dated Dec. 3, 2019 from International Application No. PCT/US2019/046439.

* cited by examiner

*Primary Examiner* — Julianna N Harvey

(57) ABSTRACT

A surgical implant and a method for the making the surgical implant is provided. The surgical implant includes various granules incorporated into an upper surface and a lower surface of a body portion thereof. The granules can be pressed into the upper surface and the lower surface via physical force using at least one mold portion. The physical force applied by the at least one mold portion can deform and/or extrude the upper surface and the lower surface to impregnate these surfaces with the granules. The granules can provide the implant with bioresorbable and/or mechanically-reinforced properties.

20 Claims, 4 Drawing Sheets

POROUS SURGICAL IMPLANT AND METHOD OF MAKING SAME

FIELD

The present technology is generally related to a surgical implant and a method of making the surgical implant incorporating bioresorbable and/or mechanically-reinforced properties, where granules incorporated into the surgical implant are used to provide the bioresorbable and/or mechanically-reinforced properties.

BACKGROUND

Surgical implants have been used in the human body to aid repair of anatomical deficiencies such as a damaged vertebral columns and broken bones. When such surgical implants are used, it is typical to rely on fasteners and/or interactions of the implants themselves with surrounding anatomical structures to hold the surgical implants in position in the body. For example, spinal implants can include surface structures or surface roughenings for interacting with the surrounding anatomical structures to hold the spinal implants in position in the body. To illustrate, such surface structures or surface roughenings could afford insertion and resist migration of the spinal implants in a disc space between adjacent vertebral bodies. However, given the need to prevent migration of surgical implants in the body, there is a need for further ways to prevent migration that do not interfere with insertion of such implants.

SUMMARY

The techniques of this disclosure generally relate to a surgical implant and method for making the surgical that incorporates granules made of a material or materials different from the surgical implant and method of making the surgical implant.

In one aspect, the present disclosure provides a method of forming a spinal implant for implantation into a human body, the method including providing a spinal implant workpiece having a first end surface, an opposite second end surface, a first lateral side surface, an opposite second lateral side surface, an upper surface, and a lower surface; providing at least one mold portion including at least one surface configured for contacting at least one of the first end surface, the second end surface, the first lateral side surface, the second lateral side surface, the upper surface, and the lower surface, the at least one surface of the at least one mold portion including surface structures for correspondingly creating surface structures on the at least one of the first end surface, the second end surface, the first lateral side surface, the second lateral side surface, the upper surface, and the lower surface; positioning granules between the at least one surface of the at least one mold portion and at least one of the first end surface, the second end surface, the first lateral side surface, the second lateral side surface, the upper surface, and the lower surface; heating the at least one mold portion and/or the spinal implant workpiece; pressing the granules via physical force of the at least one surface of the at least one mold portion against the at least one of the first end surface, the second end surface, the first lateral side surface, the second lateral side surface, the upper surface, and the lower surface to incorporate the granules into the spinal implant workpiece so that the granules extend from the at least one of the first end surface, the second end surface, the first lateral side surface, the second lateral side surface, the upper surface, and the lower surface into the spinal implant workpiece; and forming a surface configuration on the at least one of the first end surface, the second end surface, the first lateral side surface, the second lateral side surface, the upper surface, and the lower surface corresponding to the surface structures formed on the at least one surface of the at least one mold portion.

In another aspect, the disclosure provides a method of forming a spinal implant for implantation into a human body, the method including providing a spinal implant workpiece having at least one work surface formed thereon; providing at least one mold portion including at least one surface configured for contacting the at least one work surface, the at least one surface of the at least one mold portion including surface structures for correspondingly creating surface structures on the at least one work surface; positioning granules between the at least one surface of the at least one mold portion and at least one work surface; heating the at least one mold portion and/or the at least one work surface of the spinal implant workpiece; pressing the granules via physical force of the at least one surface of the at least one mold portion against the at least one work surface to incorporate the granules into the spinal implant workpiece; and forming a surface configuration on the at least one work surface using the at least one mold portion.

In yet another aspect, the disclosure provides a spinal implant for insertion into a disc space between adjacent vertebral bodies, the spinal implant including a body portion having a first end surface, an opposite second end surface, a first lateral side surface, an opposite second lateral side surface, an upper surface, and an opposite lower surface, the first lateral side surface and the second lateral side surface extending between the first end surface and the second end surface, and the upper surface and the lower surface extending between the first end surface and the second end surface; where portions of the upper surface and the lower surface each include surface structures or surface roughenings for contacting an endplate of one of the adjacent vertebral bodies to prevent migration of the spinal implant after implantation into the disc space; and where the body portion includes granules physically forced into one of the first end surface, the second end surface, the first lateral side surface, the second lateral side surface, the upper surface, and the lower surface, the granules extending from the one of the first end surface, the second end surface, the first lateral side surface, the second lateral side surface, the upper surface, and the lower surface into the body portion, the granules being formed of a bioresorbable material affording resorption of the granules after implantation of the spinal implant into the disc space.

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION

An implant according to a preferred embodiment of the present disclosure is generally indicated by the numeral 10 in FIGS. 1 and 4-7. As depicted in FIGS. 1 and 4-7, the implant 10 can be an interbody spinal fusion implant, but the present disclosure is not limited to such an application. Implants according to the present disclosure can be used throughout the body where there is a need for an implant having, for example, bioresorbable and/or mechanically-reinforced properties. As discussed below, the implant 10 can incorporate granules to provide bioresorbable and/or mechanically-reinforced properties.

Figure 1:
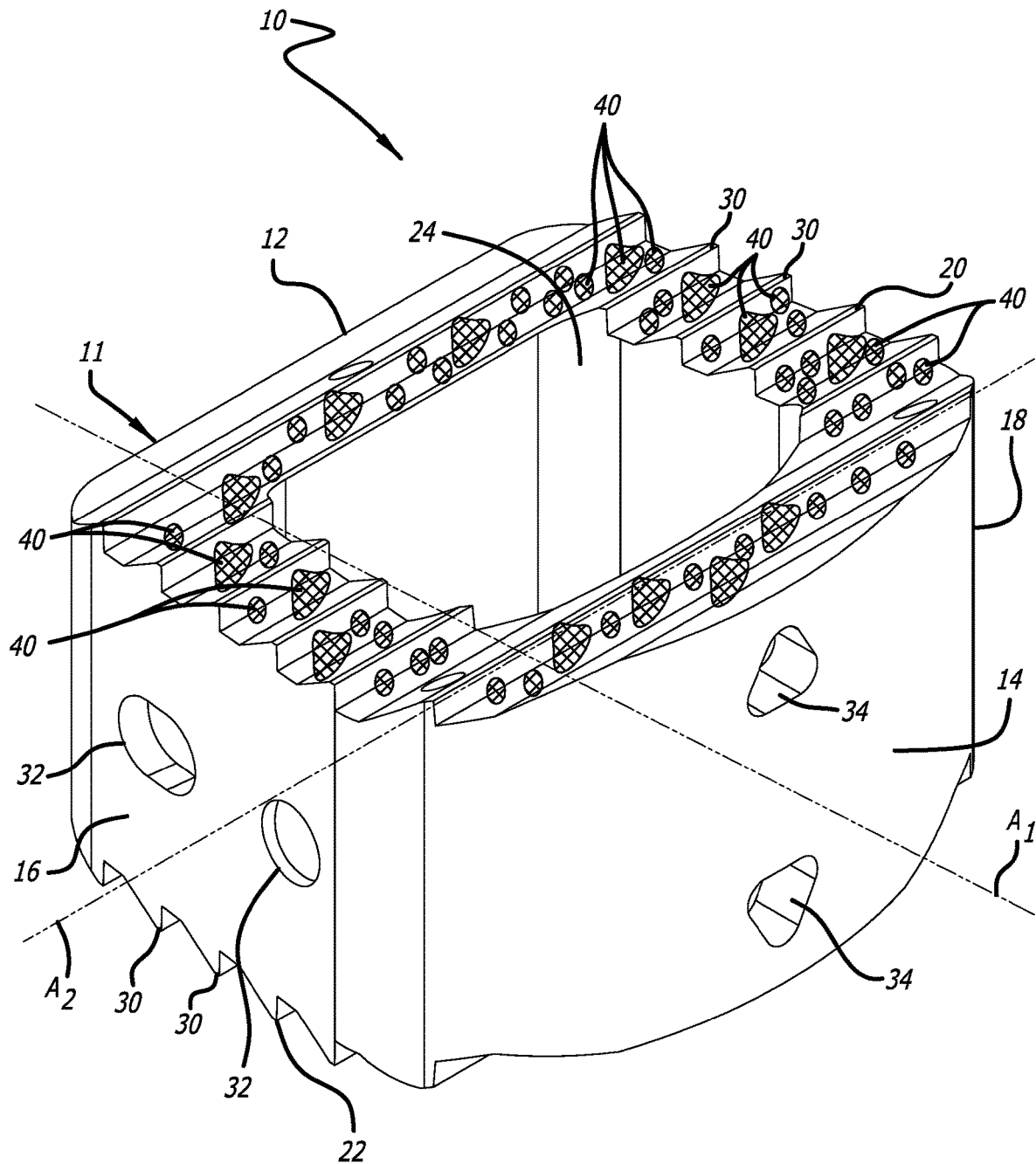
FIG. 1 is a top perspective view that illustrates a spinal implant including granules incorporated therein.

As depicted in FIG. 1 the implant 10 is configured for insertion into a disc space between adjacent vertebral bodies. The implant 10 includes a body portion 11 having a first end surface 12 and a second end surface 14, and a length between the first end surface 12 and the second end surface 14 along a first central axis $A_1$ extending through the first end surface 12 and the second end surface 14. Furthermore, the body portion 11 of the implant 10 includes a first lateral side surface 16 and a second lateral side surface 18, and a length between the first lateral side surface 16 and the second lateral side surface 18 along a second central axis $A_2$ extending through the first lateral side surface 16 and the second lateral side surface 18.

Additionally, as depicted in FIG. 1, the body portion 11 of the implant 10 includes an upper surface 20 and a lower surface 22, and an aperture 24 extending through the body portion 11 between the upper surface 20 and the lower surface 22. The aperture 24 can receive bone ingrowth and can be filled with bone growth promoting substances to promote such bone ingrowth.

The first end surface 12, the second end surface 14, the first lateral side surface 16, the second lateral side surface 18, the upper surface 20, and the lower surface 22 can include portions that are flattened and/or smoothly or sharply contoured with various convexities, concavities, and/or other surface structures or surface roughenings. Furthermore, the first end surface 12, the second end surface 14, the first lateral side surface 16, the second lateral side surface 18, the upper surface 20, and the lower surface 22 can be arranged at various angles with respect to one another. The flats, contours, surface structures, and/or angles of these surfaces can be configured to complimentarily interface with anatomical structures.

As depicted in FIG. 1, for example, the first end surface 12, the first lateral side surface 16, and the second lateral side surface 18 have flattened surfaces; the second end surface 14 has a smoothly-contoured convex surface; and the upper surface 20 and the lower surface 22 have various protrusions (or surface roughenings) 30. The protrusions 30 formed on the upper surface 20 and the lower surface 22 afford insertion and resist migration of the implant 10 in the disc space. As such, given the orientation thereof, the protrusions 30 are oriented such that the first end surface 12 is the leading end and the second end surface 14 is the trailing end during insertion into the disc space. However, the upper surface 20 and the lower surface 22 can include protrusions oppositely oriented from the protrusions 30 so that the leading end and the trailing end are reversed.

As discussed above, the implant 10 includes the aperture 24. The aperture 24 can be sized to receive bone-growth promoting materials therein facilitating bone growth through the implant 10 between adjacent vertebral bodies. The implant 10 can include additional apertures formed through the first end surface 12, the second end surface 14, the first lateral side surface 16, and the second lateral side surface 18, and these apertures, for example, can be used to facilitate attachment of instrumentation and/or facilitate bone growth therethrough. To illustrate, the first lateral side surface 16 can include apertures 32 that can be duplicated on the second lateral side surface 18, and the second end surface 14 can include apertures 34 that also can be duplicated on the first end surface 12.

The implant 10 can be formed from various materials including metals, polymers, ceramics, biologics, and/or other bioresorbable or non-bioresorbable materials. These materials can be porous, and the porosity thereof can facilitate bone ingrowth. To illustrate, the body portion 11 can be formed of one or more of these materials, and granules 40, as depicted in FIG. 1, of different ones of these materials can be incorporated into the body portion 11. The granules 40, for example, can be sized from 100 to 1000 microns, and have uniform or irregular shapes. In a preferred embodiment of the present disclosure, for example, the body portion 11 of the implant 10 can be formed from PEEK (polyether ether ketone), and, for example, the granules 40 incorporated in the body portion 11 can be formed of organic and/or inorganic minerals found in bone. The granules 40 can provide bioresorbable and/or mechanically-reinforced properties to the body portion 11.

Figure 2:
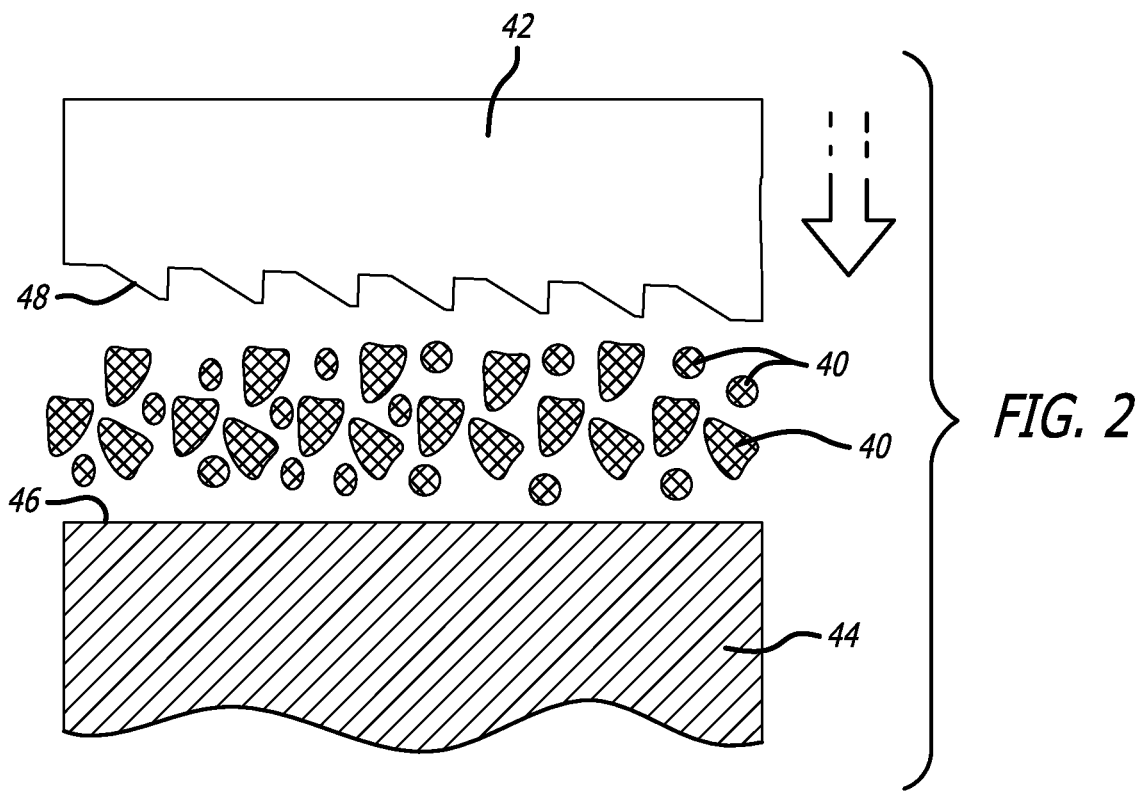
FIG. 2 is a representative side elevational view that illustrates a first part of a process used to incorporate the granules in a portion of the spinal implant of FIG. 1.
Figure 3:
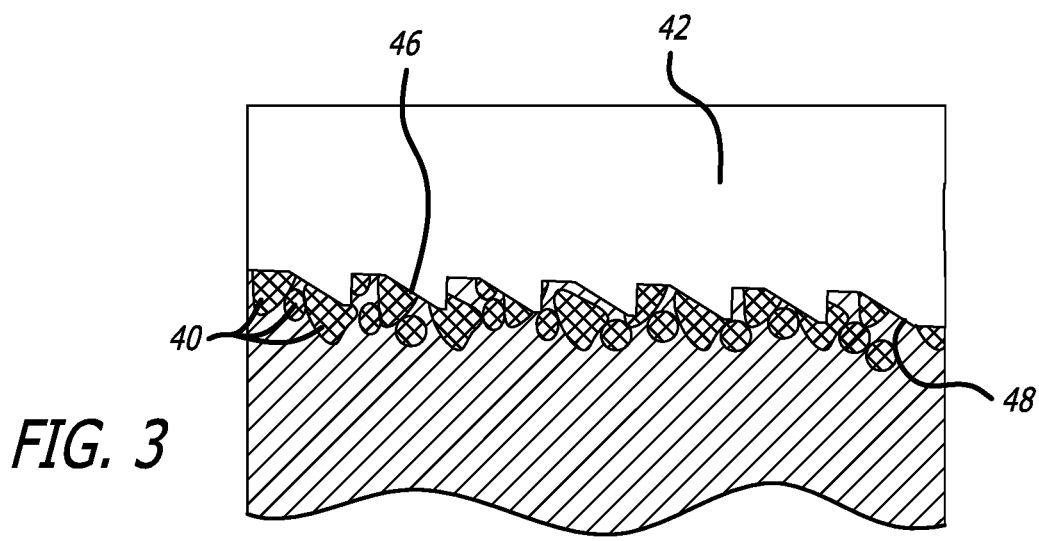
FIG. 3 is a representative side elevational view that illustrates a second part of a process used to incorporate the granules in the portion of the spinal implant of FIG. 1.
Figure 4:
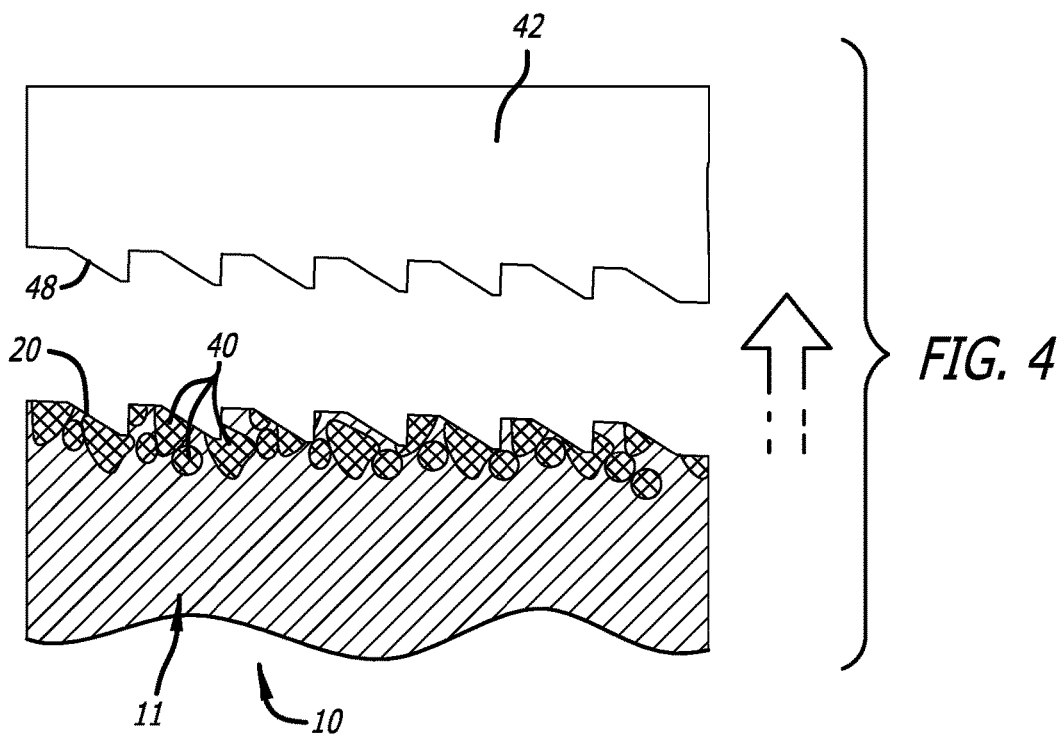
FIG. 4 is a representative side elevational view that illustrates a third part of a process used to incorporate the granules in the portion of the spinal implant of FIG. 1.

Preferably, the granules 40 can be pressed into the various surfaces of the body portion 11 using a physical process, and such impregnation of the granules 40 into the body portion 11 can occur during and/or after a molding process forming much (if not all) of the final shape of the body portion. To illustrate, as depicted in FIGS. 2-4, a mold portion 42 is used to press via physical force the granules 40 into a workpiece 44 that ultimately forms the body portion 11 of the implant 10. The workpiece 44 is the body portion 11 in an unfinished form, and the mold portion 42 used to physically force the granules 40 into the workpiece 44 can also be used in forming the final form of the body portion 11. In doing so, an upper surface 46 of the workpiece 44 is acted upon by the mold portion 42 to deform and/or extrude the upper surface 46 by impregnating the granules 40 into and through the upper surface 46, and deform and/or extrude the upper surface 46 into the shape dictated by the shape of the mold 42. In a preferred embodiment, the mold portion 42 is heated via either an internal or an external heat source to facilitate this process, but the mold portion 42 could also be unheated during this process.

As depicted in FIGS. 2-4, the mold portion 42 include at least one work surface including surface structures 48 that are used to correspondingly create the protrusions 30 formed in the upper surface 20 of the body portion 11. The work surface of the mold portion 42 also could be provided with surface structures for correspondingly creating surface configurations/structures on the upper surface 20 that include portions that are flattened and/or smoothly or sharply contoured with various convexities, concavities, and/or other surface structures or surface roughenings. While the mold portion 42 depicted in FIGS. 2-4 is used in forming the final form of the upper surface 20 (FIG. 4), the mold portion 42 or other molds can be used in similar fashion to form the final form of the various surfaces of the body portion 11.

During use of the mold portion 42, for example, the granules 40 can be positioned adjacent the upper surface 46 of the workpiece 44, and the mold portion 42 is contacted to the granules 40 and the upper surface 46 of the workpiece 44. The upper surface 46 thus is formed according to the shape of the surface structures 48 of the mold portion 42, and the granules are pressed into and through the upper surface 46 to form the upper surface 20 of the body portion 11.

The workpiece 44 could include another surface or surfaces in which the granules can be impregnated. For example, the workpiece 44 could include a lower surface (not shown) for receiving the granules 40 therein to form the lower surface 22 of the body portion 11. Furthermore, a second portion (not shown) of the mold portion 42 or another mold or molds (not shown) can be used to physically force the granules 40 into the lower surface of the workpiece 44. As such, the granules 40 can be positioned adjacent the lower surface of the workpiece 44, and the second portion of the mold portion 42 or another mold are contacted to the granules 40 and the lower surface of the workpiece 44. The lower surface of the workpiece 44 thus is formed according to the shape of surface structures (not shown) of the second portion of the mold portion 42 or another mold, and the granules are pressed into and through the lower surface of the workpiece 44 to form the lower surface 22 of the body portion 11.

In another preferred embodiment, the mold portion 42 can be used after the workpiece 44 is preshaped to form the shape of the body portion 11. To illustrate, the workpiece 44 could be machined and/or molded to form the shape of the body portion 11, and thereafter, the mold portion 42 could be used to facilitate impregnation of the granules 40 into the preshaped workpiece 44. A second portion (not shown) of the mold portion 42 or another mold or molds (not shown) can be similarly used to impregnate the granules 40 into another surface of the preshaped workpiece 44. And in yet another preferred embodiment, the workpiece 44 can be impregnated with the granules 40 prior to machining and/or molding to form the shape or the body portion 11.

If the material forming the workpiece 44 is a thermoplastic polymer such as PEEK, the mold portion 42 or the other above-discussed molds are preferably heated, and the material or materials used for granules 40 are selected to withstand the heat of the mold portion 42. The mold portion 42 can be heated via applying an external heat source or an internal heat source thereto, and the temperature of the mold portion 42 should afford making the PEEK of the workpiece 44 somewhat malleable without melting the workpiece 44. That is, the mold portion 42 could be heated above the glass transition temperature of a thermoplastic polymer forming the workpiece 44. Increasing the malleability of the workpiece 44 can make it easier to deform and/or extrude the upper surface 46 by impregnating the granules 40 into and through the upper surface 46, and deform and/or extrude the upper surface 46 into the shape dictated by the shape of the mold 42 to form the upper surface 20. Additionally, the workpiece 44 and/or the granules 40 could be preheated prior to use of the mold portion 42 or the other above-discussed molds to facilitate impregnation, and the preheated workpiece 44 and/or the preheated granules 40 could be used with a heated or unheated mold portion 42. Furthermore, after such impregnation, the workpiece 44 (or the body portion 11) could be processed via heat treatment to restore mechanical properties that may have been lost during the impregnation.

Figure 5:
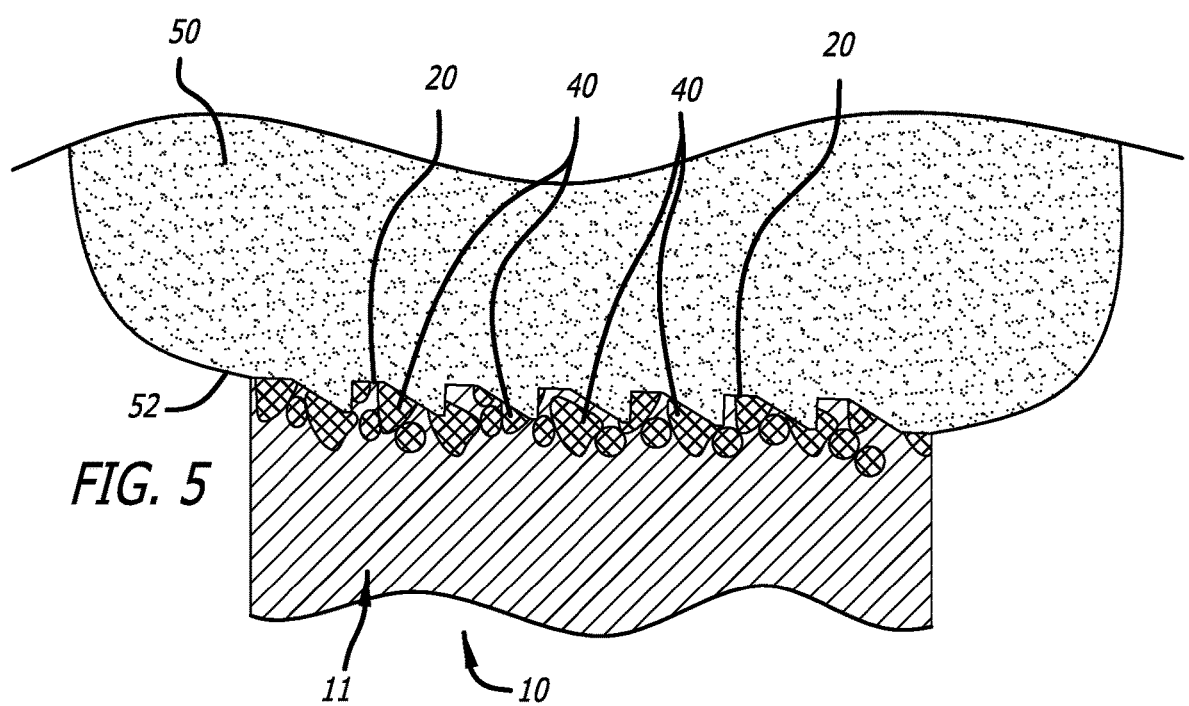
FIG. 5 is a side elevational view that illustrates a portion of the spinal implant of FIG. 1 inserted into a disc space.
Figure 6:
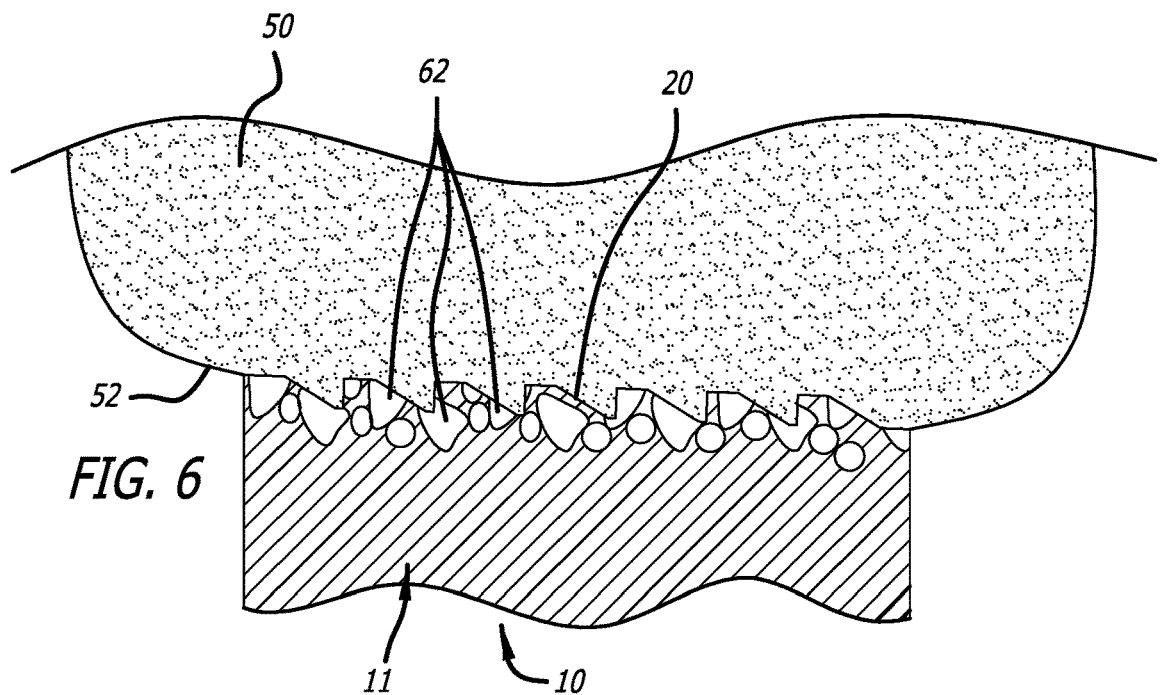
FIG. 6 is a side elevational view similar to FIG. 5 that illustrates the implant after the granules have been resorbed to form voids in the implant.
Figure 7:
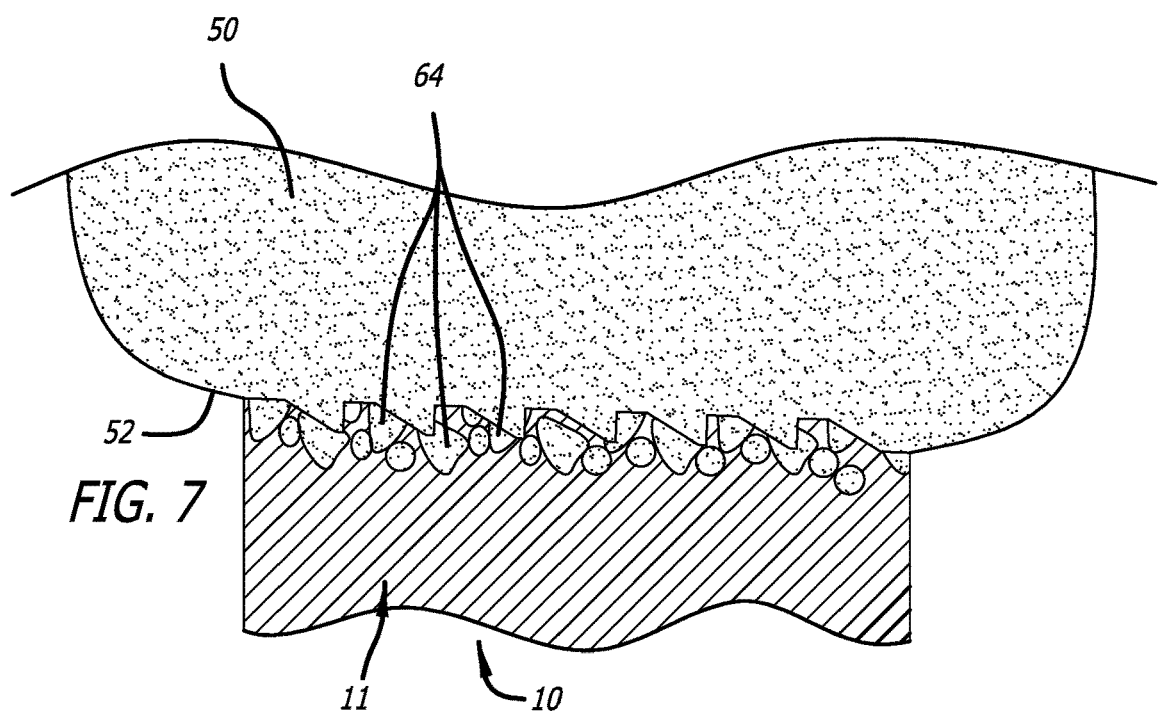
FIG. 7 is a side elevational view similar to FIG. 5 that illustrates the implant after the granules have been resorbed and bone has formed in the implant.

As depicted in FIG. 1, many of the granules 40 incorporated into the body portion 11 are incorporated into and/or communicating with the upper surface 20. As discussed above, the various surfaces of the body portion 11 can also include granules 40 similarly situated. As depicted in FIGS. 5-7, when the implant 10 is inserted into the disc space between the adjacent vertebral body, the upper surface 20 is contacted with an upper vertebral body 50 of the adjacent vertebral bodies. Specifically, as depicted in FIG. 6, the upper surface 20 and the granules 40 incorporated into and/or communicating with the upper surface 20 are contacted with a lower surface 52 of the upper vertebral body 50. If the granules 40 were selected for being bioresorbable, the granules 40 are resorbed by the body. Spaces 60 formerly filled by the granules 40 left by the resorption thereof can either be voids 62 (FIG. 6) or filled with bone 64 (FIG. 7). Either way, the voids 62 or the bone 64 can be used to prevent migration of the spinal implant 10 in the disc space. To illustrate, the voids 62 allow the bone of the lower surface (or endplate) 52 to settle therein to prevent movement of the spinal implant 10, and the bone 64 serves in physically joining the implant 10 to the lower surface 52 to prevent movement of the spinal implant 10. Alternatively, a dissolution process can be used to remove at least some of the granules 44 from the implant 10 prior to implantation, and the resulting at least partially-porous implant 10 can then be implanted. Such a dissolution process can include soaking the workpiece 44 in an acid base to remove at least some of the granules 44.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

What is claimed is:

1. A method of forming a spinal implant for implantation into a human body, the method comprising:

providing a spinal implant workpiece having a first end surface, an opposite second end surface, a first lateral side surface, an opposite second lateral side surface, an upper surface, and a lower surface;

providing at least one mold portion including at least one surface configured for contacting at least one of the first end surface, the second end surface, the first lateral side surface, the second lateral side surface, the upper surface, and the lower surface, the at least one surface of the at least one mold portion including surface structures for correspondingly creating surface structures on the at least one of the first end surface, the second end surface, the first lateral side surface, the second lateral side surface, the upper surface, and the lower surface;

positioning granules between the at least one surface of the at least one mold portion and at least one of the first end surface, the second end surface, the first lateral side surface, the second lateral side surface, the upper surface, and the lower surface;

heating the at least one mold portion and/or the spinal implant workpiece;

pressing the granules against and into at least one work surface of the spinal implant workpiece via physical force of the at least one surface of the at least one mold portion applied to the granules so that the granules extend from the at least one of the first end surface, the second end surface, the first lateral side surface, the second lateral side surface, the upper surface, and the lower surface into the spinal implant workpiece; and as the granules are being pressed into the spinal implant workpiece, forming a surface configuration on the at least one of the first end surface, the second end surface, the first lateral side surface, the second lateral side surface, the upper surface, and the lower surface corresponding to the surface structures formed on the at least one surface of the at least one mold portion via the physical force of the least one surface of the at least one mold portion applied thereto.

2. The method of claim 1, wherein the granules are formed of a bioresorbable material affording resorption of the granules after implantation of the spinal implant into the human body.

3. The method of claim 1, wherein, after implantation and resorption of the granules, spaces in the spinal implant workpiece formerly occupied by the granules are voids or bone fill.

4. The method of claim 1, wherein the surface configuration on the at least one of the first end surface, the second end surface, the first lateral side surface, the second lateral side surface, the upper surface, and the lower surface is formed by deforming and/or extruding the spinal implant workpiece using the at least one mold portion.

5. The method of claim 1, wherein the granules of the spinal implant are formed from at least one of organic and inorganic minerals found in bone.

6. The method of claim 5, wherein the granules are sized from 100 to 1000 microns.

7. The method of claim 6, wherein the granules have uniform or irregular shapes.

8. The method of claim 7, wherein the spinal implant workpiece of the spinal implant is formed from at least one of metals, polymers, ceramics, biologics, and/or other bioresorbable or non-bioresorbable materials.

9. A method of forming a spinal implant for implantation into a human body, the method comprising:

providing a spinal implant workpiece having at least one work surface formed thereon;

providing at least one mold portion including at least one surface configured for contacting the at least one work surface, the at least one surface of the at least one mold portion including surface structures for correspondingly creating surface structures on the at least one work surface;

positioning granules between the at least one surface of the at least one mold portion and the at least one work surface;

heating the at least one mold portion and/or the at least one work surface of the spinal implant workpiece;

pressing the granules against and into the at least one work surface via physical force of the at least one surface of the at least one mold portion applied to the granules to incorporate the granules into the spinal implant workpiece; and as the granules are being pressed into the spinal implant workpiece, forming a surface configuration on the at least one work surface via the physical force of the at least one surface of the at least one mold portion against the at least one work surface.

10. The method of claim 9, wherein the granules are formed of a bioresorbable material affording resorption of the granules after implantation of the spinal implant into the human body.

11. The method of claim 10, wherein the granules are sized from 100 to 1000 microns.

12. The method of claim 11, wherein the granules have uniform or irregular shapes.

13. The method of claim 9, wherein the surface configuration on the at least one work surface is formed by deforming and/or extruding the spinal implant workpiece using the at least one mold portion.

14. The method of claim 9, wherein the granules of the spinal implant are formed from at least one of organic and inorganic minerals found in bone.

15. A method of forming a spinal implant for implantation into a human body, the method comprising:

providing a spinal implant workpiece having at least one work surface formed thereon;

providing at least one mold portion including at least one surface configured for contacting the at least one work surface, the at least one surface of the at least one mold portion including surface structures for correspondingly creating surface structures on the at least one work surface;

positioning granules between the at least one surface of the at least one mold portion and the at least one work surface;

heating the at least one mold portion and/or the at least one work surface of the spinal implant workpiece; and simultaneously, pressing the granules against and into the at least one work surface via physical force of the at least one surface of the at least one mold portion applied to the granules, and forming a surface configuration on the at least one work surface via the physical force of the at least one surface of the at least one mold portion applied against the at least one work surface.

16. The method of claim 15, wherein the granules are formed of a bioresorbable material affording resorption of the granules after implantation of the spinal implant into the human body.

17. The method of claim 15, wherein the granules are sized from 100 to 1000 microns.

18. The method of claim 15, wherein the granules have uniform or irregular shapes.

19. The method of claim 15, wherein the surface configuration on the at least one work surface is formed by deforming and/or extruding the spinal implant workpiece using the at least one mold portion.

20. The method of claim 15, wherein the granules of the spinal implant are formed from at least one of organic and inorganic minerals found in bone.

* * * * *